(12) United States Patent
Elmaanaoui et al.

(10) Patent No.: US 12,714,286 B2
(45) Date of Patent: Aug. 25, 2026

(54) IMAGE ACQUISITION AT ACCURATE START WAVELENGTH

(71) Applicant: Canon U.S.A., Inc., Melville, NY (US)

(72) Inventors: Badr Elmaanaoui, Belmont, MA (US); Leonid Pesok, Watertown, MA (US); Mostafa Raziq, Saugus, MA (US)

(73) Assignee: Canon U.S.A., Inc., Melville, NY (US)

( * ) Notice: Subject to any disclaimer, the term of this patent is extended or adjusted under 35 U.S.C. 154(b) by 645 days.

(21) Appl. No.: 18/158,801

(22) Filed: Jan. 24, 2023

(65) Prior Publication Data

US 2024/0245281 A1 Jul. 25, 2024

(51) Int. Cl.

| | |
|---|---|
| ***A61B 1/00*** | (2006.01) |
| ***A61B 1/045*** | (2006.01) |
| ***A61B 1/06*** | (2006.01) |
| ***A61B 1/07*** | (2006.01) |
| ***A61B 1/313*** | (2006.01) |
| ***G01J 1/44*** | (2006.01) |

(52) U.S. Cl.

CPC .......... *A61B 1/00006* (2013.01); *A61B 1/045* (2013.01); *A61B 1/0655* (2022.02); *A61B 1/07* (2013.01); *A61B 1/3137* (2013.01); *G01J 1/44* (2013.01)

(58) Field of Classification Search

CPC ... A61B 1/00006; A61B 1/045; A61B 1/0655; A61B 1/07; A61B 1/3137; A61B 5/0066; G01J 1/44; G01B 9/02004; G01B 9/02091

See application file for complete search history.

(56) References Cited

U.S. PATENT DOCUMENTS

| | | | | |
|---|---|---|---|---|
| 8,379,297 | B2 | 2/2013 | Taverner | |
| 9,052,179 | B2 | 6/2015 | Inoue et al. | |
| 9,595,804 | B2 | 3/2017 | Minneman et al. | |
| 10,016,124 | B2 | 7/2018 | Moriguchi et al. | |
| 10,729,327 | B2 | 8/2020 | Adamson et al. | |
| 10,788,310 | B2 | 9/2020 | Wang et al. | |
| 11,262,185 | B2 | 3/2022 | Huber et al. | |
| 11,397,076 | B2 | 7/2022 | Aebischer et al. | |
| 2017/0241763 | A1* | 8/2017 | Wang ................. | G01B 9/02078 |
| 2021/0164853 | A1* | 6/2021 | Vez .................... | G01B 9/02007 |

(Continued)

OTHER PUBLICATIONS

Baran, A.S.; Koen, C.; Pokrzywka, B.; "A detection threshold in the amplitude spectra calculated from Kepler data obtained during K2 mission"; Oxford University Press on behalf of the Royal Astronomical Society, 2014, 17 pages.

(Continued)

*Primary Examiner* — Monica T Taba

(74) *Attorney, Agent, or Firm* — Canon U.S.A., Inc. I.P. Division

(57) ABSTRACT

A wavelength interrogation apparatus includes an optical fiber with a fiber core and an interference pattern in the fiber core, one or more photodiodes or photo-sensors to convert from a transmittance light of the optical fiber to an electrical signal, and an electrical circuit to generate a pulse with a predetermined duration, wherein the apparatus provides image acquisition at accurate start wavelength. The electrical circuit can include a first amplifier, a first differentiator or high-pass filter, a comparator, and a multivibrator, and can include other components.

18 Claims, 14 Drawing Sheets

(56) References Cited

U.S. PATENT DOCUMENTS

2023/0184622 A1* 6/2023 Alfataierge ............ G01L 25/00
356/73.1

OTHER PUBLICATIONS

Poddar, Raju; Kim, Dae Yu; Werner, John S.; Zawadzki, Robert J.; "Improved in vivo imaging of human blood circulation . . . "; Opthalmic Technologies XXIV, edited by Fabrice Manns, Per G. Soderberg, Arthur Ho, Proc. of SPIE vol. 8930, 89300X, 2014, 9 pages.

* cited by examiner

IMAGE ACQUISITION AT ACCURATE START WAVELENGTH

BACKGROUND

Field

The present disclosure generally relates to image acquisition and, more particularly, to image acquisition at accurate start wavelength.

Description of the Related Art

Optical coherence tomography (OCT) forms images of an object by detecting interference between a reference beam of light and a detected beam of light that has been reflected back from a sample target. Some of the reflected light is used to measure the light or wavelength via interrogation or wavelength interrogation. A swept-source OCT (SS-OCT) apparatus uses a tunable light source that changes wavelengths and performs scanning using a wavelength of light along illuminated measurement points. OCT signals can be uniformly sampled in time during scanning.

There is uncertainty of positioning the sampling times with respect to the start of the scan, and various techniques are used to know when an OCT scan begins.

For example, a drive signal for a swept source laser filter can be used to determine start of scan, i.e. start wavelength for acquisition. This is deficient because it is prone to variations in the mechanical response of the laser scan mechanism.

An amplitude based threshold from a portion of the light source output spectrum is commonly used. This is deficient because it is prone to amplitude light source long term and short term power output variations. This is also prone to spectrum variation, temperature stability, etc.

A wavelength based filter can be used to determine a laser wavelength and then adjust for the scan. A fiber Bragg grating (FBG), for example, can be used in reflection mode with a circulator or coupler to capture a narrow peak for start of wavelength. This is deficient because it uses more fiber optical components and uses more light for triggering hence less light for imaging. It also does not necessarily compensate for thermal drift.

Today's wavelength interrogation is based on converting laser power via a photodiode to an amplitude power monitor signal with respect to time. The photodetector output signal is then compared to a fix threshold value. A pulse is generated when the monitored laser amplitude power is higher than the threshold set value. Because the laser power fluctuates over time, hence amplitude changes, this method is not stable and precise. In addition, the amplitude signal changes over time due to the temperature variation on the laser, causing the wavelength start time to vary.

Wavelength interrogation can also use an FBG sensor. FBGs are nanometer periodical refractive index changes engraved in an optical fiber core. When a broadband light spectrum is injected in the fiber, via an optical circulator, this optical signal will interact with the FBG, where the wavelengths that fulfill its resonation condition are reflected (1% optical power for example), while the others are transmitted (99% of optical power for example). The reflected spectrum is centered at the Bragg wavelength whereas in the transmitted signal a suppression can be seen at the same wavelength. However, circulators have limited bandwidth and typically can have significant loss at the desired trigger wavelength, for example, at or about 1360 nm or at or about 1260 nm. The FBG operates on the analysis of the reflected signal and the drawback of this interrogation is high cost and complexity to setup, and bandwidth reduction due to the power fluctuation over time. To compensate for the power loss, an increase of input power is required. This results in lower power for sample interrogation, and causes artifact(s) in the image.

It would be beneficial to overcome these concerns and mitigate against uncertainty of positioning the sampling times with respect to the start of a scan.

SUMMARY

The present disclosure provides image acquisition at accurate start wavelength and enhances wavelength interrogation, thereby reducing wavelength complexity and cost, and mitigating against uncertainty of positioning the sampling times with respect to the start of a scan.

According to some embodiments, a wavelength interrogation apparatus includes an optical fiber with a fiber core and an interference pattern in the fiber core, one or more photodiodes or photo-sensors to convert from a transmittance light of the optical fiber to an electrical signal, and an electrical circuit to generate a pulse with a predetermined duration, wherein the apparatus provides image acquisition at accurate start wavelength. The electrical circuit can include a first amplifier, a first differentiator or high-pass filter, a comparator, and a multivibrator, and can include other components.

The first differentiator can include a differentiator amplifier configured to take a derivative of a signal and produces an output proportional to how fast an input is changing. The first differentiator can include a high pass filter and charge pump amplifier configured to filter signals above a cut-off point frequency and generate short pulses at the output. The comparator determines whether an input has reached a predetermined value by comparing two voltages and outputting either a one (1) or a zero (0). The multivibrator is configured to monitor a voltage on a capacitor and start a timer on every rising edge. The first amplifier can include a transimpedance amplifier configured to maintain stability by converting output current to a voltage formatted as a usable signal output. The transimpedance amplifier can include at least an op-amp, a feedback resister, a feedback capacitor, and can include other components. The feedback capacitor provides a low-pass filter to attenuate noise. The transimpedance amplifier can further include a resister divider to bias amplifier input above ground. The optical fiber can include a fiber Bragg grating, and the wavelength interrogation apparatus can be part of a hermetically sealed temperature controlled package.

According to some embodiments, an intravascular imaging apparatus can include a light source, an interferometer, a scanner, and a wavelength interrogator that has an optical fiber with a fiber core and an interference pattern in the fiber core, a first amplifier, a first differentiator or high-pass filter, a comparator, and a multivibrator, wherein the intravascular apparatus provides image acquisition at accurate start wavelength.

According to some embodiments, a wavelength interrogation method can include converting optical power from an input light source into an electrical current, converting output current of photodiodes to a voltage formatted as a usable signal, taking a derivative of a signal and producing an output proportional to how fast the input is changing, determining whether an input has reached a predetermined value by comparing two voltages and outputting either a one (1) or a zero (0), monitoring a voltage on a capacitor, and starting a timer on every rising edge.

According to some embodiments, a non-transitory storage medium storing a program for causing a computer to execute a wavelength interrogation method can include converting optical power from an input light source into an electrical current, converting output current of photodiodes to a voltage formatted as a usable signal, taking a derivative of a signal and producing an output proportional to how fast the input is changing, determining whether an input has reached a predetermined value by comparing two voltages and outputting either a one (1) or a zero (0), monitoring a voltage on a capacitor, and starting a timer on every rising edge.

Further features, objects, and advantages of the present disclosure will become apparent from the following description of exemplary embodiments with reference to the attached drawings, where like structure is indicated with like reference numerals.

DESCRIPTION OF THE EMBODIMENTS

Figure 1:
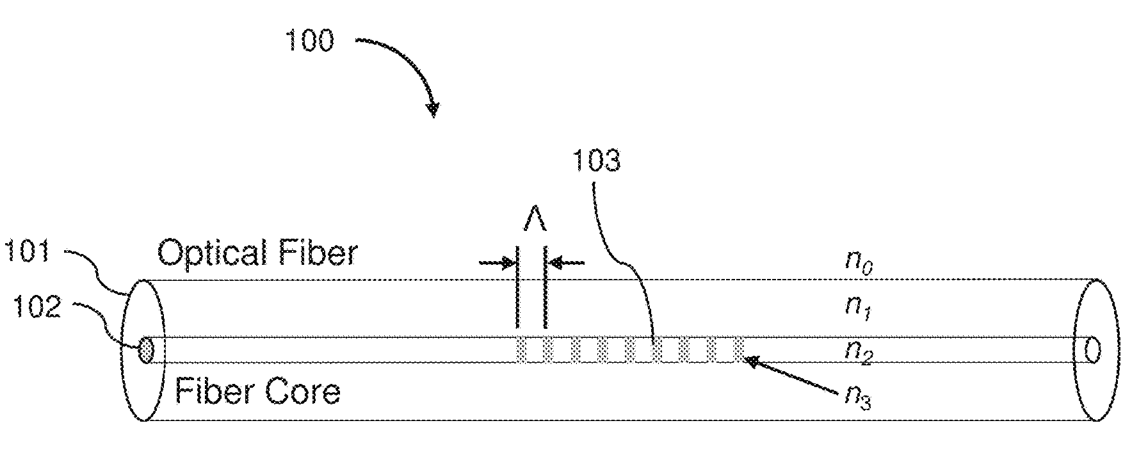
FIG. 1 illustrates FBG structure and wavelength migration.
Figure 1:
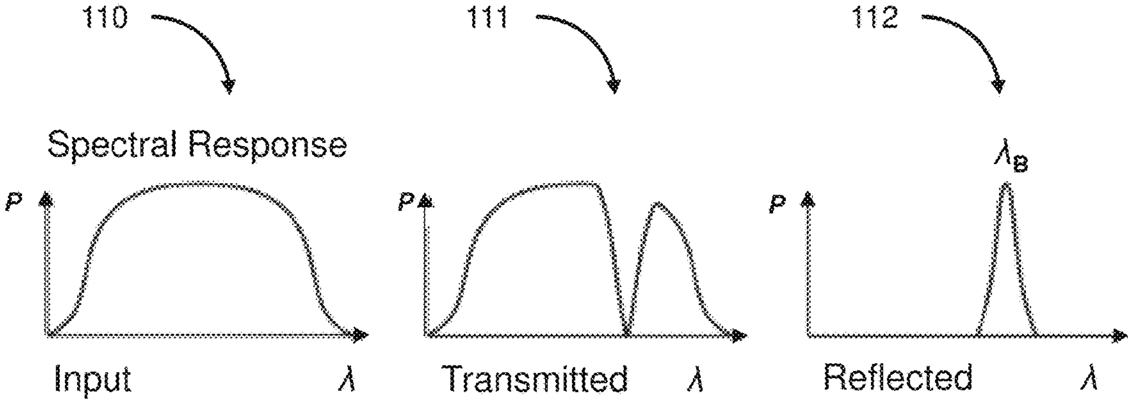

Various exemplary embodiments, features, and aspects of the disclosure will be described with reference to the drawings that relate to medical devices, apparatuses, methods, and storage mediums to provide image acquisition at accurate start wavelength and enhance wavelength interrogation, thereby reducing wavelength complexity and cost, and mitigating against uncertainty of positioning the sampling times with respect to the start of a scan, and may have different characteristics, advantages, disadvantages, performance parameters, or the like.

In the following embodiments, wavelength interrogation configurations are described that may functionally interact with a medical device or continuum robot, robotic or snake catheter assembly with a rotational drive assembly or other actuator to impart rotational movement to a guide wire of a steerable catheter, endoscope, or other flexible medical device or surgical tool. The guide wire can include one or more drive wires, support wires, or other types of wires, and the drive assembly can drive bendable sections of the catheter by pushing and/or pulling the driving wires in a push/pull or insertion/pulling-out direction. The drive assembly is releasably connected to the steerable catheter and a breakaway mechanism can be used so the drive assembly disconnects from the catheter in response to a breakaway force.

Some embodiments functionally implement intravascular imaging modalities including optical coherence tomography (OCT), swept source OCT (SS-OCT), optical frequency domain imaging (OFDI), Fourier domain OCT (FD-OCT), spectral domain OCT (SD-OCT), time domain OCT (TD-OCT), multi-modality OCT (MMOCT), angiography, near infrared auto fluorescence (NIRAF), spectrally encoded endoscopy (SEE), ultrasound imaging (US), intravascular ultrasound (IVUS), computed tomography (CT), magnetic resonance imaging (MRI), other imaging modalities, combinations or hybrids thereof. Arrangements can also functionally implement light detection and ranging (LiDAR) configurations that are used to measure distances to remote targets. The present disclosure is not limited to any particular configuration.

An OCT configuration or arrangement according to some embodiments can include a swept laser light source, interferometer, spectrometer, scanner, optics, electronics, and can include other components or combinations thereof. The spectrometer can include microelectromechanical components (MEMS), where MEMS scanning mirrors can be used. The OCT arrangement can be an SS-OCT or another type of OCT configuration.

SS-OCT is an OCT technique of acquiring the spectral distribution of the interference light by time division, and spectral domain OCT is an OCT technique of acquiring the spectral distribution of the interference light by space division.

SS-OCT imaging is performed by splitting light emitted from a wavelength tunable light source into measurement light and reference light, superposing the return light of the measurement light returned from a sample with the reference light to generate interference light, detecting the interference light with a photodetector, and applying Fourier transform and other processes to the detected data acquired according to the wavelength sweeping and the measurement light scanning.

SS-OCT generates tunable or swept optical signal on an optical fiber that is transmitted to an interferometer. The swept optical signal scans over a scan band with a narrowband emission.

The present disclosure provides image acquisition at accurate start wavelength and enhances wavelength interrogation, thereby reducing wavelength complexity and cost, and mitigating against uncertainty of positioning the sampling times with respect to the start of a scan.

FIG. 1 illustrates FBG structure 100 and wavelength migration according to some embodiments.

The FBG structure 100 has an optical fiber 101 with a fiber core 102. An interference pattern 103 with periodic variations in the refractive index is inscribed in the fiber core 102. The interference pattern 103 reflects particular wavelengths and transmits all others. The periodicity Λ of the FBG structure 100 corresponds to the index of refraction variation and $$n_0, n_1, n_2, n_3, \ldots n_n$$

correspond to the index change. The FBG structure 100 can have uniform periodicity, and the grating structure can be uniform, chirped, tilted, or other structure. The ability to accurately present and maintain the grating wavelength is a fundamental feature and advantage of fiber Bragg gratings.

The wavelength migration illustrates the spectral response 110 of the input wavelength, the spectral response 111 of the transmitted wavelength, and the spectral response 112 of the reflected wavelength. Broadband light is injected in the FBG structure 100 and the transmitted and reflected power spectrums 111, 112 show where a narrow spectral width is reflected back at the Bragg wavelength $\lambda_B$ by the grating of the FBR structure 100.

The principal function of the FBG structure 100 is when light from a broadband source is launched on the grating plane, one spectral wavelength component which satisfies the phase-matching conditions is reflected back, and the other wavelength components are transmitted through. Therefore, the FBG structure 100 can be used to block certain wavelengths of interest from transmitting. Transmitted light from the FBG structure 100 can be incident on one or more photodiodes, photo-sensors, or other components.

A small portion of the main OCT laser output power can be diverted and be used for FBG interrogation to measure and detect the frequency of interest.

Figure 2:
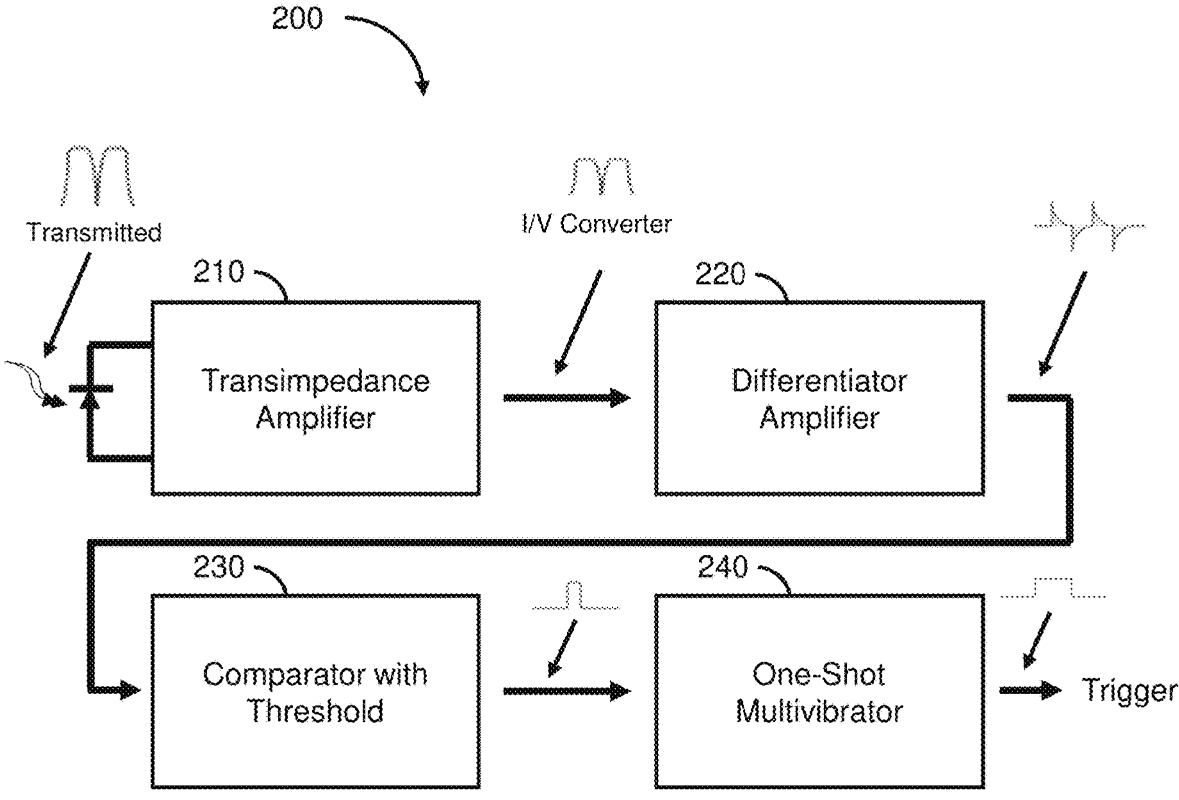
FIG. 2 illustrates an FBG signal processing block diagram based on a differentiator amplifier.

FIG. 2 shows an FBG signal processing arrangement 200 using the FBG structure 100 of FIG. 1 based on a differentiator amplifier according to some embodiments. One or more photodiodes, photo-sensors, or other components convert the optical power from the reference transmitted FBG into an electrical current.

The FBG signal processing arrangement 200 includes a transimpedance amplifier 210, a differentiator amplifier 220, a comparator 230, a multivibrator 240, and can include other components or combinations thereof. The FBG signal processing arrangement 200 does not use any optic circulator to reduce components and complexity of wavelength interrogation. One or more photodiodes or photo-sensors converts the optical power from an input light signal into an electrical current.

The transimpedance amplifier 210 converts output current of photodiodes or other components to a voltage formatted as a usable signal output. The differentiator amplifier 220 takes a derivative of the signal and produces an output proportional to how fast the input is changing. The comparator 230 determines whether an input has reached a predetermined value by comparing two voltages and outputting either a one (1) or a zero (0). The multivibrator 240 is a one-shot multivibrator that monitors the voltage on a capacitor and generates a trigger to start a timer on every rising edge.

Figure 3:
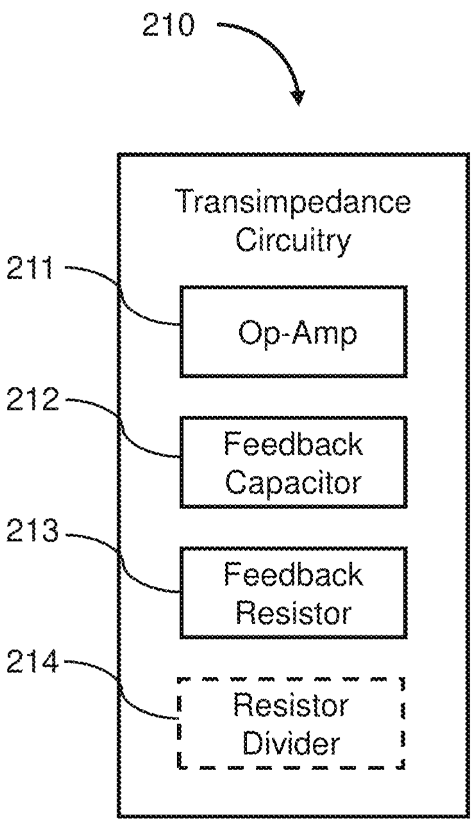
FIG. 3 illustrates a transimpedance circuitry block diagram.

The transimpedance amplifier 210 is a photovoltaic transimpedance amplifier and can amplify light-dependent current of photodiodes for processing. As shown in FIG. 3, the transimpedance amplifier 210 has transimpedance circuitry including one or more of an operational amplifier (op-amp) 211, a feedback capacitor 212, a feedback resistor 213, and can include other components or combinations thereof. The feedback capacitor 212 compensates for the photodiode capacitance and provides a first-order low-pass filter that attenuates high-frequency noise. In order to improve the amplifier's response time, a resister divider 214 can be used to bias the amplifier input above ground.

Figure 4:
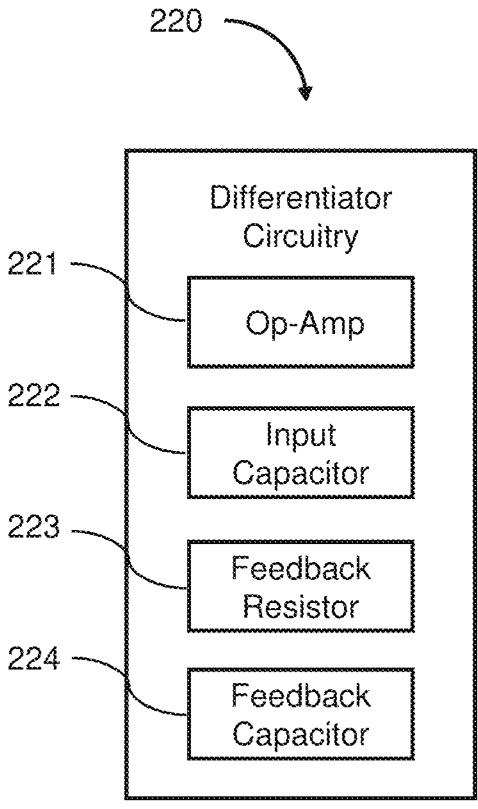
FIG. 4 illustrates a differentiator circuitry block diagram.

The output from the transimpedance circuitry is fed to the differentiator amplifier 220. As shown in FIG. 4, the differentiator amplifier 220 has differentiator circuitry including one or more of an op-amp 221, an input capacitor 222, a feedback resister 223, a feedback capacitor 224, and can include other components or combinations thereof. The differentiator amplifier 220 inverts the output from the transimpedance circuitry with the input capacitor 222. Hence, the differentiator output is inverted relative to the polarity of the FBG transmitted signal. The input capacitor 222 is used to block a direct current (DC) signal and allows alternating current (AC) input voltage changes to pass through. To stabilize the differentiator circuitry at high-frequency signals, the feedback capacitor 224 is added across the differentiator feedback resistor 223. This then forms an active high pass filter (HPF). HPF output pulses are the FBG electrical signals that are modulated by the dynamical wavelength variation.

The output signal from the differentiator amplifier 220 goes through the comparator 230 to compare this incoming signal with a pre-set or predetermined threshold reference voltage and produces an output pulse signal based on this voltage comparison.

The output of the comparator 230 pulse triggers one-shot timer circuitry through the one-shot multivibrator 240. The timer generates a pulse with a predetermined duration in which the duration of this pulse is determined by a resistor-capacitor (RC) network connected externally. The one-shot timer pulse can then be used as an A-line trigger for OCT acquisition.

The FBG signal processing arrangement 200 can be part of a hermetically sealed temperature controlled package according to some embodiments. This can prove advantageous and important for applications that need precise acquisition at an exact predetermined start wavelength without drift due to temperature change, which can be non-negligible in a case the FBG is used in a non-temperature controlled environment.

Some embodiments have advantageous features including a less complex optic setup due to optic circulator elimination that reduces components and complexity of wavelength interrogation, the transmission wavelength interrogation is less prone to mechanical response, precise, and repeatable. Wavelength interrogation with the FGB signal processing arrangement 200 reduces overall wavelength interrogation cost and makes wavelength interrogation configurations cheap to build.

The FBG signal processing arrangement 200 improves and is advantageous over known FBG arrangements in that it has easy electronic integration, is less complex due to optic circulator elimination, is less immune to electromagnetic interference, and can be used for single fixed-wavelength FBG interrogation by configuring the fiber core to reflect a specific wavelength.

Figure 5:
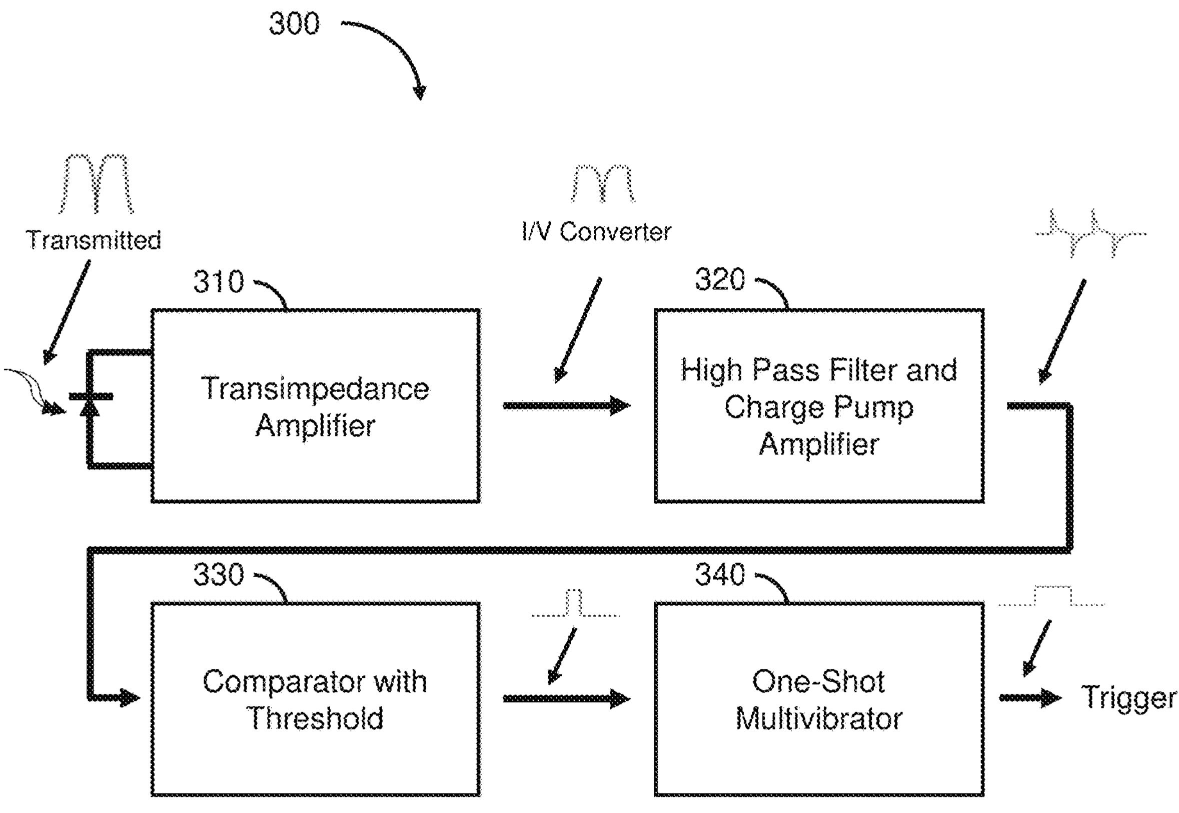
FIG. 5 illustrates an FBG signal processing block diagram based on a high pass filter and a charge pump amplifier.

The differentiator amplifier 220 in FIG. 2 can be replaced by HPF and charge pump amplifier circuitries, as shown in FIG. 5, before the signal is fed to the comparator with threshold and to the one-shot multivibrator.

The FBG signal processing arrangement 300 of FIG. 5 uses the FBG structure 100 of FIG. 1 based on an HPF and charge pump amplifier according to some embodiments. The FBG signal processing arrangement 300 does not use any optic circulator to reduce components and complexity of wavelength interrogation. A photodiode converts the optical power from the reference transmitted FBG into an electrical current.

The FBG signal processing arrangement 300 includes a transimpedance amplifier 310, an HPF and charge pump amplifier 320, a comparator 330, a multivibrator 340, and can include other components or combinations thereof. A photodiode converts the optical power from an input light signal into an electrical current.

The transimpedance amplifier 310 converts output current of photodiodes or other components to a voltage formatted as a usable signal output. The HPF and charge pump amplifier 320 filters signals above a cut-off or predetermined point frequency and generates short pulses at the output. The comparator 330 determines whether an input has reached a predetermined value by comparing two voltages and outputting either a one (1) or a zero (0). The multivibrator 340 is a one-shot multivibrator that monitors the voltage on a capacitor and generates a trigger to start a timer on every rising edge.

Figure 6:
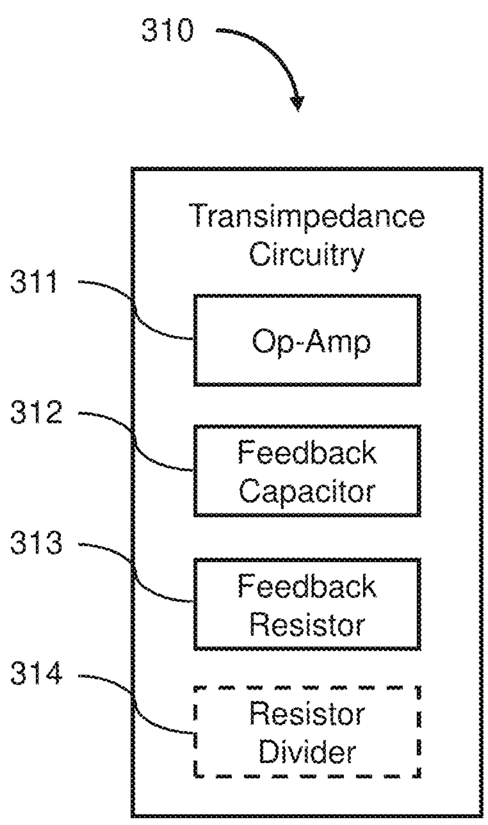
FIG. 6 illustrates a transimpedance circuitry block diagram.

The transimpedance amplifier 310 is a photovoltaic transimpedance amplifier and can amplify light-dependent current of photodiodes for processing. As shown in FIG. 6, the amplifier 310 has transimpedance circuitry including one or more of an op-amp 311, a feedback capacitor 312, a feedback resistor 313, and can include other components or combinations thereof. The feedback capacitor 312 compensates for the photodiode capacitance and provides a first-order low-pass filter that attenuates high-frequency noise. In order to improve the amplifier's response time, a resister divider 314 can be used to bias the amplifier input above ground.

The output from the transimpedance circuitry is fed to the HPF and charge pump amplifier 320. The HPF filter passes signals above a cut-off or predetermined point frequency and generates short pulses, determined by a time constant resistor-capacitor (RC), at the output. The charge pump amplifies the HPF output signals that are modulated by the dynamical wavelength variation.

The output signal from the HPF and charge pump amplifier 320 goes through the comparator 330 to compare this incoming signal with a pre-set or predetermined threshold reference voltage and produces an output pulse signal based on this voltage comparison.

The output of the comparator 330 pulse triggers one-shot timer circuitry through the one-shot multivibrator 340. The timer generates a pulse with a predetermined duration in which the duration of this pulse is determined by an RC network connected externally. The one-shot timer pulse can then be used as an A-line trigger for OCT acquisition.

The FBG signal processing arrangement 300 can be part of a hermetically sealed temperature controlled package according to some embodiments. This can prove advantageous and important for applications that need precise acquisition at the exact desired start wavelength without drift due to temperature change, which can be non-negligible in a case the FBG is used in a non-temperature controlled environment.

Some embodiments have advantageous features including a less complex optic setup due to optic circulator elimination that reduces components and complexity of wavelength interrogation, the transmission wavelength interrogation is less prone to mechanical response, precise, and repeatable. Wavelength interrogation with the FGB signal processing arrangement 300 reduces overall wavelength interrogation cost and makes the wavelength interrogation cheap to build.

The FBG signal processing arrangement 300 improves and is advantageous over known FBG arrangements in that it has easy electronic integration, is less complex due to optic circulator elimination, is less immune to electromagnetic interference, and can be used for single-fixed-wavelength FBG interrogation by configuring the fiber core to reflect a specific wavelength.

FBG and wavelength interrogation arrangements as described above can functionally implement various intravascular OCT imaging modalities according to some embodiments including SS-OCT, for example.

Figure 7:
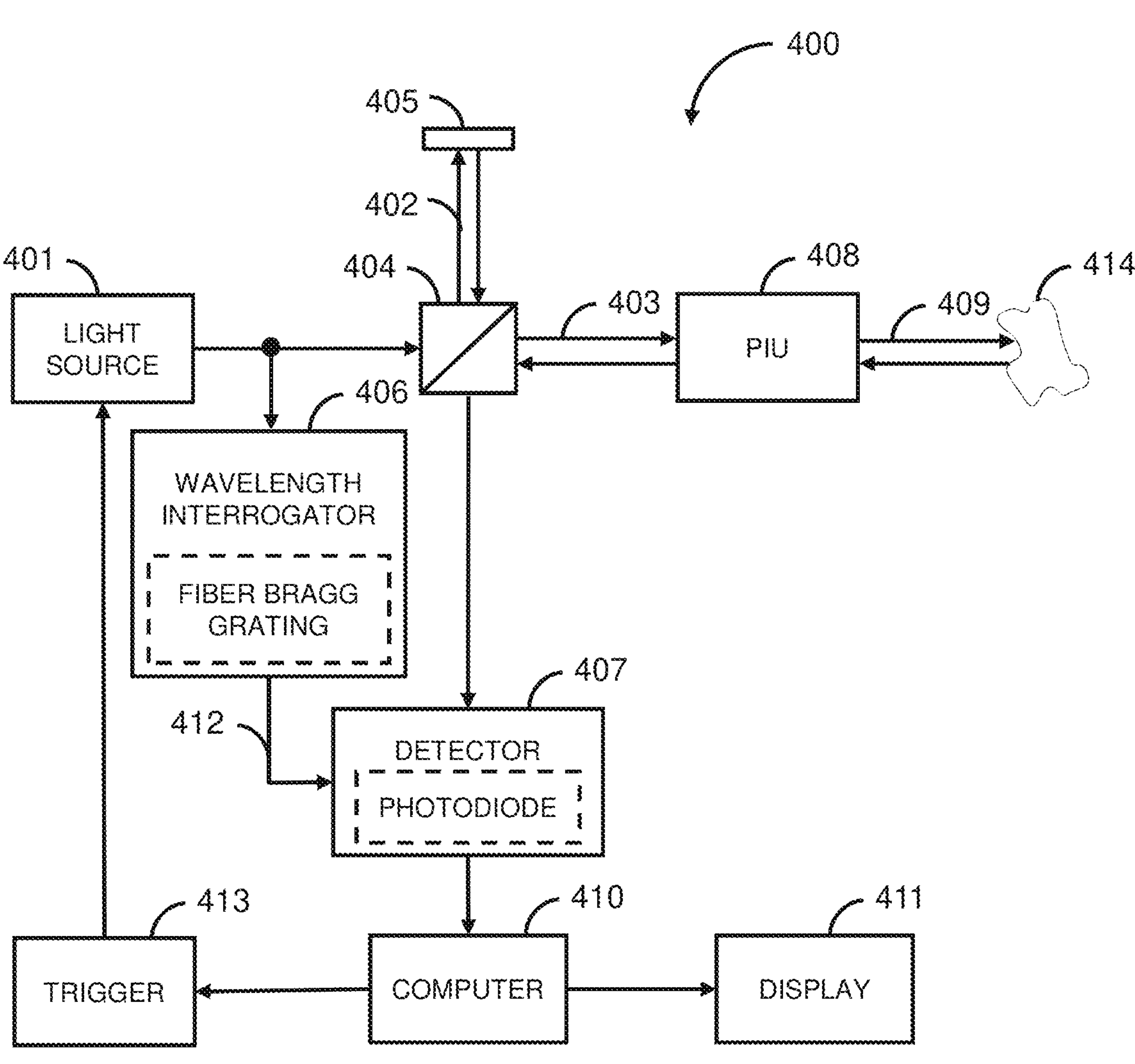
FIG. 7 illustrates an SS-OCT apparatus.
Figure 8:
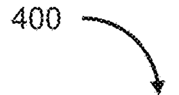
FIG. 8 illustrates a block diagram of the SS-OCT apparatus of FIG. 7.
Figure 8:
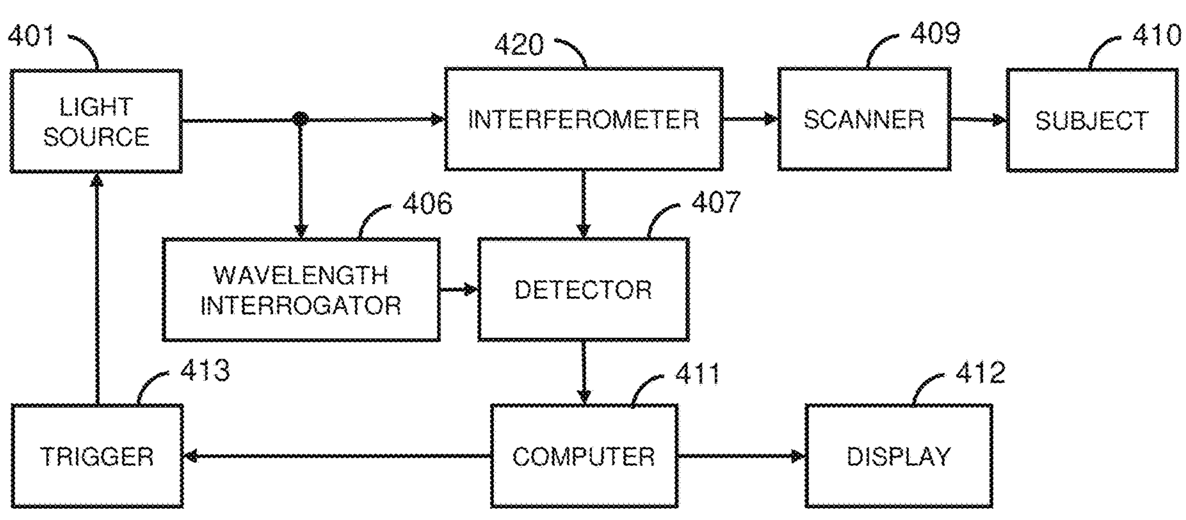

FIGS. 7 and 8 illustrate an exemplary hardware configuration and block diagram of an SS-OCT apparatus 400 including FBG and wavelength interrogation features as described above according to some embodiments. Other intravascular or OCT imaging configurations can also implemented.

Figure 10:
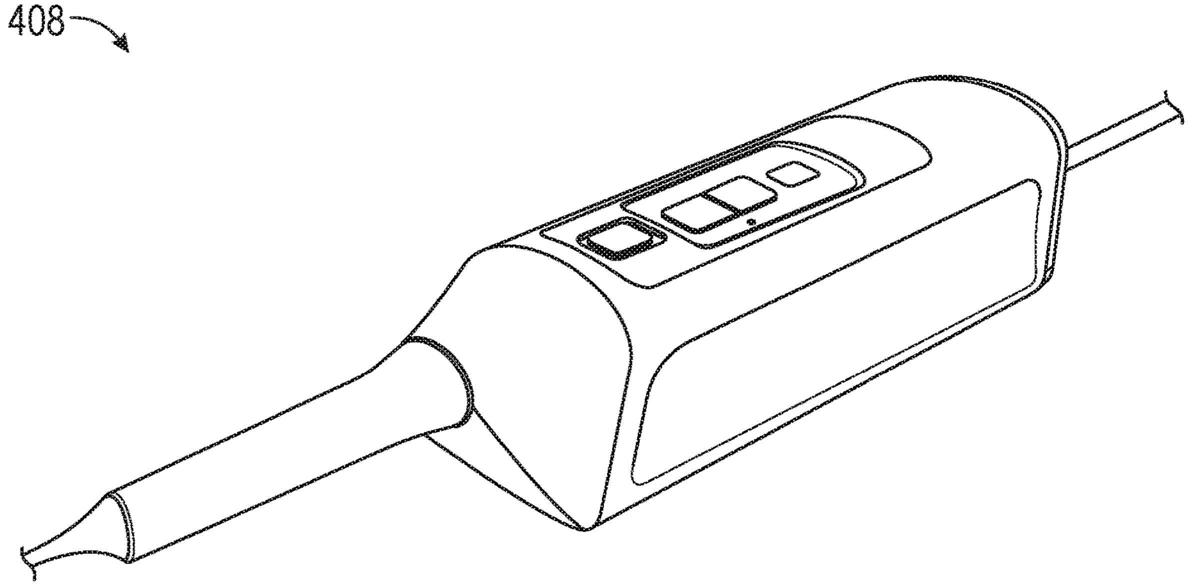
FIG. 10 illustrates a PIU.
Figure 11:
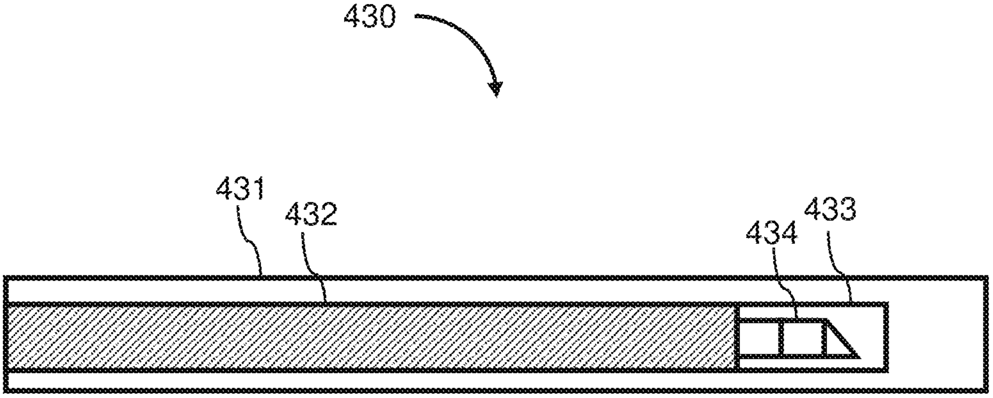
FIG. 11 illustrates a catheter.

The SS-OCT apparatus 400 includes a light source 401, a reference arm 402, a sample arm 403, a beam splitter 404, a reference mirror 405, a wavelength interrogator 406, a detector or measurement device 407, a patient interface unit (PIU) 408, a scanner or probe 409, a computer 410, a display 411, and can include other components or combinations thereof, where some together are herein referred to as an interferometer. The wavelength interrogator 406 receives and modulates light received from the light source 401 and generates an output signal 412 to the detector 407, and the detector 407 generates a trigger or clock signal 413 that causes the light source 401 to start a sweep with an accurate start wavelength at a new scanning position. The PIU 408 is shown in FIG. 10 and can provide functions including imaging core rotation, imaging core translation, optical probe engage/unlock, user interface, or combinations thereof. The scanner (probe) 409 can be an optical probe including a catheter, an endoscope, or other probe, and is illustrated in FIG. 11 as a catheter 430. The apparatus 400 interacts with a sample, target, or other object 414.

The light source 401 can be a tunable light source that changes wavelength and generates a measurement beam, the detector 407 measures the measurement beam, and the scanner (probe) 409 moves the measurement beam on the sample 414.

The SS-OCT apparatus 400 can perform imaging based on wavelength sweeping and measurement light scanning, wherein the imaging can be performed by splitting light emitted from the light source 401 into measurement light and reference light, superimposing the return light of the measurement light returned from the sample 414 with the reference light to generate interference light, detecting data of the interference light with the detector 407, and processing the detected data acquired according to the wavelength sweeping and the measurement light scanning.

The light source 401 sweeps at predetermined frequency (wavelength sweep rate) within a predetermined wavelength range. The light source 401 emits light to the beam splitter 404, which splits or divides the light from the light source 401 into a reference beam passing into the reference arm 402 and a measurement or sample beam passing through the sample arm 403. The wavelength interrogator 406 receives and modulates light received from the light source 401 and generates reference timing pulses to the detector 407. The reference beam is reflected from the reference mirror 405. The sample beam passes through the PIU 408 and is emitted through the scanner 409 toward the sample 414. Reflected light (scattered light) is received from the sample 414, and interference light with respect to the reference light is obtained. A tomographic image is generated based on the intensity of the light. The beam splitter 404 functions as both a light splitter and a light combiner and is positioned at an angle to the reference mirror 405, the detector 407, and to the sample 414. The light source 401 can be a laser, a white light, a broadband light, a tunable light, or other types of light.

Light reflected from the reference mirror 405 and light reflected from the sample 414 pass through the beam splitter 404 and are combined to form an interference beam that is provided to the detector 407.

The detector 407 is a photodetector or photodiode that receives the reference timing pulses from the wavelength interrogator 406, and also receives the interference beam from the beam splitter 404. The interference beam is converted from an analog signal to a digital signal using an analog to digital converter.

Scanning is started in SS-OCT by using a trigger signal that provides a wavelength scanning start timing. The trigger signal is generated at a timing in which the light is received by a photodiode, to determine the wavelength scanning start time. The A-line trigger signal indicates the timing for starting each A-line scanning, and is generated by the wavelength swept source light source driver in SS-OCT or the interference light detection device in SD-OCT.

The wavelength interrogator 406 receives and modulates light received from the light source 401 and generates an output signal 412 to the detector 407, and the detector 407 generates a trigger or clock signal 413 that causes the light source 401 to start a sweep with an accurate start wavelength at a new scanning position.

FBG signal processing arrangement of the wavelength interrogator 406 includes a transimpedance amplifier, a differentiator amplifier or an HPF and charge pump amplifier, a comparator, a multivibrator, and can include other components or combinations thereof. A photodiode converts the optical power from an input light signal into an electrical current.

The transimpedance amplifier converts output current of one or more photodiodes, photo-sensors, or other components to a voltage formatted as a usable signal output. The differentiator amplifier takes a derivative of a signal and produces an output proportional to how fast the input is changing. Alternatively, the HPF and charge pump amplifier filters signals above a cut-off point frequency and generates short pulses at the output. The comparator determines whether an input has reached a predetermined value by comparing two voltages and outputting either a one (1) or a zero (0). The multivibrator is a one-shot multivibrator that monitors the voltage on a capacitor and can start a timer on every rising edge.

The transimpedance amplifier is a photovoltaic transimpedance amplifier and can amplify light-dependent current of photodiodes for processing. The amplifier has transimpedance circuitry including one or more of op-amp, a feedback resister, a feedback capacitor, and can include other components or combinations thereof. The feedback capacitor compensates for the photodiode capacitance and provides a first-order low-pass filter that attenuates high-frequency noise. In order to improve the amplifier's response time, a resister divider can be used to bias the amplifier input above ground.

The output from the transimpedance circuitry is fed to either the differentiator amplifier or the HPF and charge pump amplifier.

In a case where the output from the transimpedance circuitry is fed to the differentiator amplifier, the differentiator amplifier inverts the output from the transimpedance circuitry with an input capacitor. Hence, the differential output is inverted relative to the polarity of the FBG transmitted signal. The input capacitor is used to block DC signal and allows AC input voltage changes to pass through. To stabilize the differentiator circuitry at high-frequency signals, a feedback capacitor can be added across a differentiator feedback resistor. This then forms an active HPF. HPF output pulses are the FBG electrical signals that are modulated by the dynamical wavelength variation.

In a case where the output from the transimpedance circuitry is fed to the HPF and charge pump amplifier, the HPF filter passes signals above a cut-off point frequency and generates short pulses, determined by a time constant RC, at the output. The charge pump amplifies the HPF output signals that are modulated by the dynamical wavelength variation.

The output signal from the differentiator amplifier or the HPF and charge pump goes through the comparator to compare this incoming signal with a pre-set or predetermined threshold reference voltage and produces an output pulse signal based on this voltage comparison.

The output of the comparator pulse triggers one-shot timer circuitry. The timer generates a pulse with a predetermined duration in which the duration of this pulse is determined by an RC network connected externally. The one-shot timer pulse can then be used as an A-line trigger for OCT acquisition.

The wavelength interrogator 406 provides advantages over known interrogators because the wavelength interrogator 406 does not include an optic circulator to reduce components and complexity of wavelength interrogation, and the transmission wavelength interrogation is less prone to mechanical response, precise, and repeatable. Wavelength interrogation with the wavelength interrogator 406 reduces overall wavelength interrogation cost and makes the wavelength interrogation cheap to build.

The wavelength interrogator 406 improves and is advantageous over known interrogators in that it has easy electronic integration, is less complex due to optic circulator elimination, is less immune to electromagnetic interference, and can be used for single-fixed-wavelength FBG interrogation by configuring the fiber core to reflect a specific wavelength.

The detector 407 generates a trigger or clock signal 413 based on the output signal 412 from the wavelength interrogator 406, and trigger signal 413 causes the light source 401 to start a sweep with an accurate start wavelength at a new scanning position.

Figure 9:
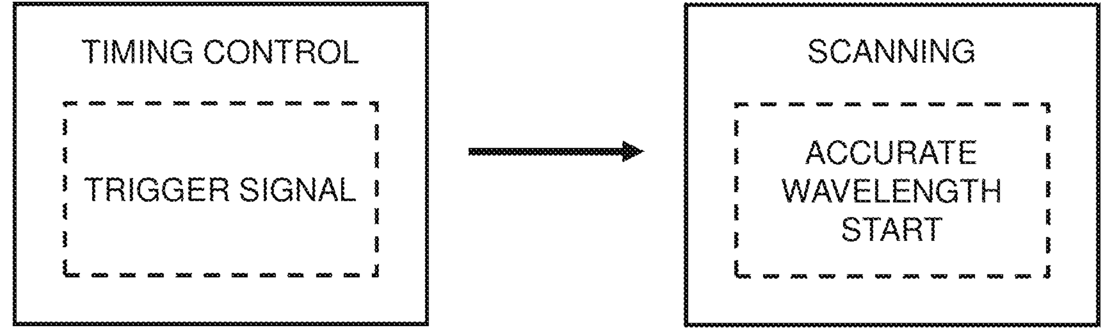
FIG. 9 illustrates timing control.

The wavelength interrogator 406 provides timing control for the SS-OCT apparatus 400 so scanning takes place at an accurate start wavelength, as shown in FIG. 9.

The sweep of wavelengths or wavelength sweeping corresponds to supplying a wavelength (or narrow wavelength band) that is adjusted as a function of time in a controlled manner. During a sweep of wavelengths, the light source 401 moves across a sweep range as the wavelength that is provided is adjusted at a sweep rate. The sweep range is a range of wavelengths to be swept, and the sweep rate corresponds to how quickly the supplied wavelength is adjusted from one wavelength to the next. The sweep range in SS-OCT can correspond to a narrow wavelength band or other wavelength band.

Longitudinal scanning is accomplished by changing the length of the reference arm 402. Longitudinal scanning provides a way of changing the location at which interference in the optical radiation is emitted off axis to the longitudinal axis of the scanner (probe) 409.

The sample arm 403 includes the PIU 408 that connects the interferometer to the probe 409. The PIU 408 is shown in FIG. 10 and can include an imaging core spin motor, a linear stage, a fiber optic combiner, a graphical user interface (GUI), circuitry or a circuit board assembly, control buttons, light emitting diodes (LEDs), and can include other components or combinations thereof. The GUI is configured to provide input/output, display results, and/or other functions. The PIU 408 is configured to provide functions including imaging core rotation, imaging core translation, optical probe engage/unlock, user interface, and/or other functions.

The scanner (probe) 409 is an optical probe that directs the sample beam to the sample 414, where the optical probe 409 can be a catheter, an endoscope, or other instrument, where rotational scanning of the probe 409 takes place with a rotational scanning device. Samples including internal organs or tissues can be viewed by the probe 409 including arteries, vessels, airway, esophagus, colon, or other samples. A rotational drive can be used to rotate the probe 409 including a rotational motor with a rotary fiber joint.

FIG. 11 shows the scanner (probe) 409 configured as a catheter 430, where the catheter 430 includes an elongate, flexible, tubular body that is configured for intravascular placement within an internal lumen. The catheter 430 is configured to rotate for circumferential scanning and includes one or more tubular members including an outer sheath 4311 and an inner sheath 432 can include other components. An illumination fiber 434 is disposed at a distal end of the inner sheath 433. A detection fiber can be disposed within the inner sheath 432. The detection fiber can be arranged within the outer sheath 431 and the outer sheath 431 is disposed around the inner sheath 432. The illumination fiber 434 and the detection fiber can be driven by one or more different motors.

The scanner (probe) 409 includes a lens for focusing which can be a gradient index (GRIN) lens, a ball lens, a spherical lens, an aspherical lens, other lenses or combinations thereof. The scanner (probe) 409 is configured as a forward-viewing or side-viewing probe. In a side-viewing probe, the incident light can be bent with respect to an optical axis of the scanner (probe) 409.

The scanner (probe) 409 includes illumination and collection optics to irradiate the sample 414 with the sample beam and to collect light that is reflected from the sample 414. This reflected or scattered light is then transmitted through the sample arm 403 back to the beam splitter 404. The reference beam is reflected from the reference mirror 405 in the reference arm 402. The sample beam is reflected or scattered from the sample 414 through scanner (probe) 409 and the PIU 408 in the sample arm 403. The reference beam and the sample beam combine or recombine at the beam splitter 404, which generates a combined or recombined beam that has an interference pattern. An interference pattern occurs when the reference arm 402 and the sample arm 403 have the same optical length.

The recombined beams or interference patterns that are output by the interferometer are continuously acquired and detected by the detector 407. The detector 407 can be one or more photodiodes, multi-array cameras, or other types of detectors. Each detector 407 measures the interference pattern(s) between the reference arm 402 and the sample arm 403. The detector 407 generates electrical signals representative of the interference pattern(s) obtained from the output of the interferometer that are converted to digital signals to be analyzed by the computer 411 and output to the display 412 where an image of the sample is obtained and can be analyzed.

Imaging is performed through SS-OCT when the interference pattern signals are produced by different scans of wavelength when reflected at different depths using low coherence interferometry. Fourier-Domain OCT calculates the depth dependent reflection profiles. Continuously performing this A-scan at different locations creates a two-dimensional cross section.

SS-OCT can use a single longitudinal mode or a multi-longitudinal mode where the depth range in the single longitudinal mode is not restricted by the cavity length of the source. SS-OCT uses a wavelength-swept laser as the light source. SS-OCT performance depends on the swept laser. SS-OCT arrangements have high imaging speed and longer imaging depth range with a single photon detector compared with other OCT arrangements. SS-OCT light sources can operate at various wavelengths including 850 nm, 1050 nm, 1310 nm, 1550 nm, or other wavelengths.

SS-OCT includes intensity-based characteristics where sweep is the optical signal generated by the laser. A sweep is defined by a monotonic increase in optical frequency from start wavelength to end wavelength which defines the sweep range as $$k = 2\pi/\lambda$$

$$\Delta\lambda = |\lambda\text{end} - \lambda\text{start}|$$

The sweep range is the optical bandwidth of the laser and is inversely proportional to the theoretically achievable axial resolution in OCT. Generally, the larger the sweep range, the better the axial resolution. The center wavelength Ac is the mean of start and end wavelength. The center wavelength represents a compromise between water absorption and scattering. For longer wavelengths, scattering decreases, but water absorption becomes more dominant. There is less scattering at longer center wavelengths, but more water absorption. The center wavelength is usually not the center of gravity of the sweep with respect to power, but the mean of start and end wavelength $\lambda_c=(\lambda_{end}+\lambda_{start})/2$.

The wavelength can have one of two directions. If the wavelength changes from short to long wavelengths over time, the sweep is generally termed “forward sweep”. If the wavelength changes from long to short wavelengths over time, the sweep is generally termed “backward sweep”. Swept lasers can produce unidirectional sweeps, or alternating forward and backward sweeps, in which case the sweep is considered bidirectional. For application in OCT, the laser normally has a repetitive sweep train with a period $T_{rep}$.

OCT speed generally refers to a depth scan rate in axial scans per second or A-scans/see with the unit of Hertz (Hz). A-scan rates have increased from a few hundred Hz to many megahertz, where OCT A-scan rates can be classified as MHz-OCT or multi-MHz-OCT. In OCT, one sweep generates a single depth profile at one sample location, the A-scan. Images are generated by stitching of those A-scans, so the OCT A-scan rate is equal to or at least directly proportional to the sweep repetition rate, which is called sweep rate $f_{sweep}=1/T_{rep}$.

The light source 401 disperses light or is incident on the sample 414 at various wavelengths. The light is within an imaging spectrum bandwidth that can be a mixture of various wavelengths in a wavelength range including infrared, ultraviolet, other ranges, and can include the entire visible spectrum. Wavelength categories, for example, can be 250-1000 nm that generally includes ultraviolet, visible, and near infrared light, 1000-3000 nm that generally includes mid-wave light, and 3000-18000 nm that generally includes thermal infrared light. OCT systems operate at different wavelengths including the infrared band within a wavelength range of 800-900 nm, the near infrared band within a wavelength range of 1250-1350 nm, or other wavelengths. The SS-OCT apparatus 100 can operate, for example, at a center wavelength of 1310 nm with a wavelength range of 100 nm (nanometer).

The light source 401 can output different wavelengths or wavelength ranges during a controlled wavelength sweep. Controlling the sweep rate may increase the useful optical energy received from the optical elements in a given interrogation time.

A sweep can be a change of parameter and can refer to a frequency sweep or a sweep of voltage. A swept sine can refer to a sine wave whose frequency is changed as a function of time.

The computer 411 includes one or more of a processor, controller, control circuitry, memory, an input and output (I/O) interface, a communication interface, or combinations thereof, and is configured to perform overall control of the SS-OCT apparatus 400. The display 412 can be a monitor, an LCD (liquid panel display), an LED (light emitting diode) display, an OLED (organic LED) display, a plasma display, an organic electro luminescence panel, or the like. Based on the control of the apparatus 400, a screen may be displayed on the display 412 showing one or more images being captured, captured images, captured moving images recorded, data or other information on the memory.

Figure 12:
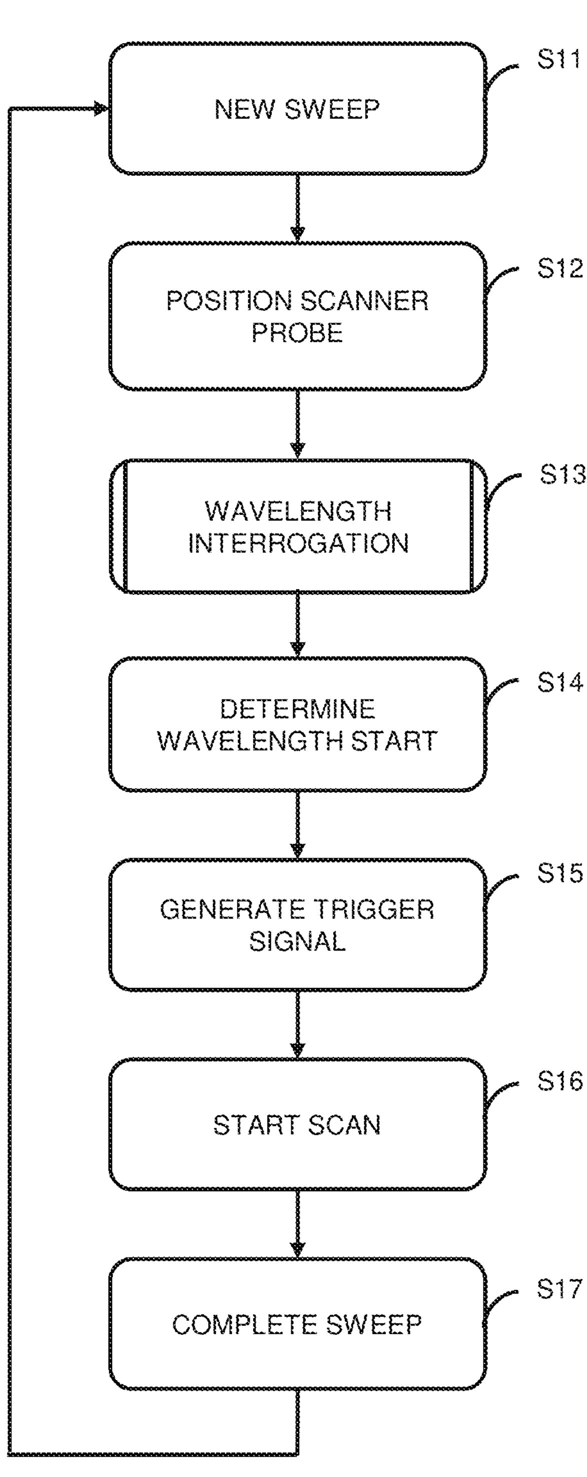
FIG. 12 illustrates a wavelength scanning method.

FIG. 12 shows a method for wavelength sweeping according to some embodiments that begins a new sweep in step S11. The scanner (probe) 409 is positioned in step S12. Wavelength interrogation takes place in step S13 to determine a wavelength start in step S14. A trigger signal is generated in step S15 and a scan starts in step S16. The scan completes in step S16 and the process returns to Step S11 to begin a new sweep.

Figure 13:
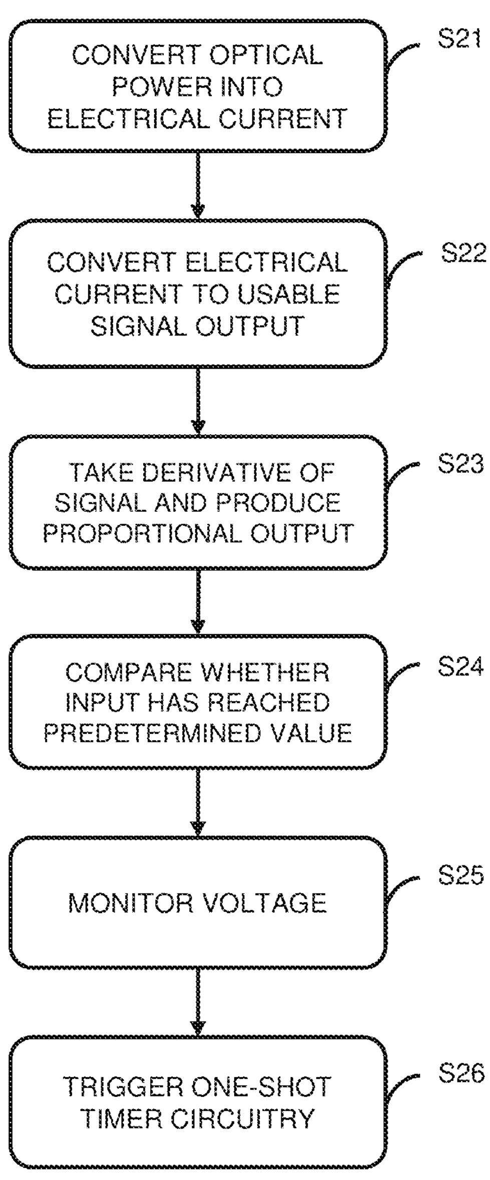
FIGS. 13 and 14 illustrate wavelength interrogation methods.

FIG. 13 shows details of the wavelength interrogation step S13 based on use of a differential amplifier. A photodiode converts the optical power from an input light signal into an electrical current in step S21. A transimpedance amplifier converts output current of photodiodes or other components to a voltage formatted as a usable signal output in step S22. In step S23, a differentiator amplifier takes a derivative of a signal and produces an output proportional to how fast the input is changing. In step S24, a comparator determines whether an input has reached a predetermined value by comparing two voltages and outputting either a one (1) or a zero (0). A one-shot multivibrator monitors the voltage on a capacitor in step S25 and can start a timer on every rising edge in step S26.

Figure 14:
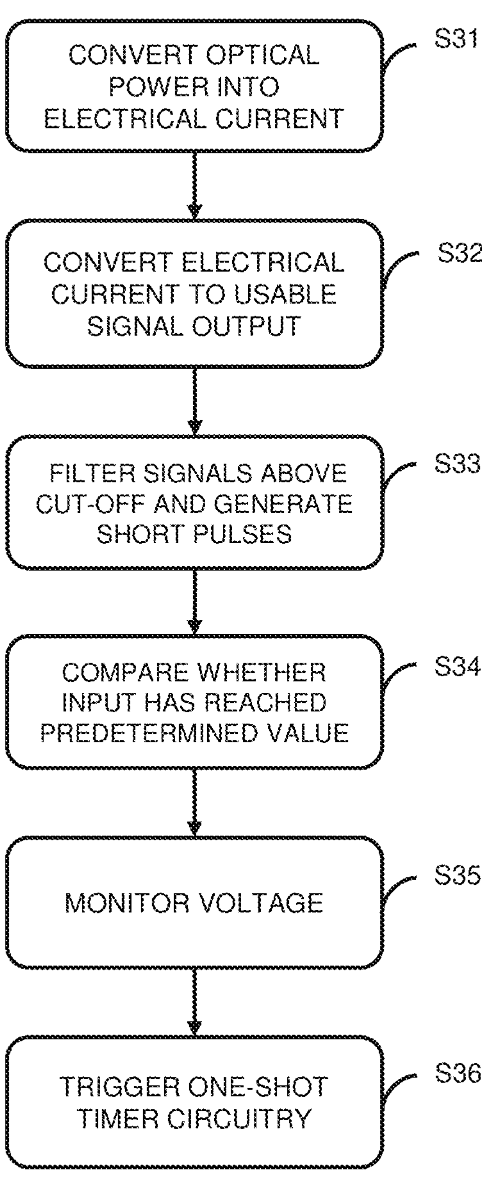

FIG. 14 shows details of the wavelength interrogation step S13 based on use of an HPF and charge pump amplifier. A photodiode converts the optical power from an input light signal into an electrical current in step S31. A transimpedance amplifier converts output current of photodiodes or other components to a voltage formatted as a usable signal output in step S32. In step S33, the HPF and charge pump amplifier filters signals above a cut-off point frequency and generates short pulses at the output. In step S34, a comparator determines whether an input has reached a predetermined value by comparing two voltages and outputting either a one (1) or a zero (0). A one-shot multivibrator monitors the voltage on a capacitor in step S35 and can start a timer on every rising edge in step S36.

Additional features or aspects of present disclosure can also advantageously implement one or more AI (artificial intelligence) or machine learning algorithms, processes, techniques, or the like, to implement image acquisition at accurate start wavelength and enhance wavelength interrogation, thereby reducing wavelength complexity and cost, and mitigating against uncertainty of positioning the sampling times with respect to the start of a scan. Such AI techniques use a neural network, a random forest algorithm, a cognitive computing system, a rules-based engine, or the like, and are trained based on a set of data to assess types of data and generate output. For example, a training algorithm can be configured to implement image acquisition at accurate start wavelength and enhance wavelength interrogation. The model(s) can be configured as software that takes images as input and returns predictions for the given images as output. The model(s) can be an instance of a model architecture (set of parameter values) that has been obtained by model training and selection using a machine learning and/or optimization algorithm/process. A model can generally include, for example, an architecture defined by a source code (e.g. a convolutional neural network including layers of parameterized convolutional kernels and activation functions, or the like) and configuration values (parameters, weights, features, or the like) that are initially set to random values and are then over the course of the training iteratively optimized given data example, an objective function (loss function), an optimization algorithm (optimizer), or the like.

At least some of the wavelength interrogator signals can be used as input data and provided to the training algorithm. Initial detected wavelength light information and data of the wavelength interrogator can be stored in a database to facilitate precise image acquisition at accurate start wavelength and enhance wavelength interrogation during an imaging procedure for new data. Through visualization guidance of wavelength interrogation that are generated using input mapping to the model(s) or through expert research, machine learning can find parameters for AI processes. The training algorithm is configured to learn physical relationships in the input data to best describe these relationships or correlations. The data sets include information based on a number of factors including, for example, the acquired wavelengths rates, patterns, or the like. The data is evaluated using a weighted evaluation where the weights are learned through a training process, through subject matter specifications, or the like. Deep learning mechanisms can augment an AI process to identify indicators in the image data that can include, for example, new wavelength start times, or the like.

According to some embodiments, a wavelength interrogation apparatus includes an optical fiber with a fiber core and an interference pattern in the fiber core, one or more photodiodes or photo-sensors to convert from a transmittance light of the optical fiber to an electrical signal, and an electrical circuit to generate a pulse with a predetermined duration, wherein the apparatus provides image acquisition at accurate start wavelength. The electrical circuit can include a first amplifier, a first differentiator or high-pass filter, a comparator, and a multivibrator, and can include other components.

The first differentiator can include a differentiator amplifier configured to take a derivative of a signal and produces an output proportional to how fast an input is changing. The first differentiator can include a high pass filter and charge pump amplifier configured to filter signals above a cut-off point frequency and generate short pulses at the output. The comparator determines whether an input has reached a predetermined value by comparing two voltages and outputting either a one (1) or a zero (0). The multivibrator is configured to monitor a voltage on a capacitor and start a timer on every rising edge. The first amplifier can include a transimpedance amplifier configured to maintain stability by converting output current to a voltage formatted as a usable signal output. The transimpedance amplifier can include at least an op-amp, a feedback resister, a feedback capacitor, and can include other components. The feedback capacitor provides a low-pass filter to attenuate noise. The transimpedance amplifier can further include a resister divider to bias amplifier input above ground. The optical fiber can include a fiber Bragg grating, and the wavelength interrogation apparatus can be part of a hermetically sealed temperature controlled package.

According to some embodiments, an intravascular imaging apparatus can include a light source, an interferometer, a scanner, and a wavelength interrogator that has an optical fiber with a fiber core and an interference pattern in the fiber core, a first amplifier, a first differentiator or high-pass filter, a comparator, and a multivibrator, wherein the intravascular apparatus provides image acquisition at accurate start wavelength.

According to some embodiments, a wavelength interrogation method can include converting optical power from an input light source into an electrical current, converting output current of photodiodes to a voltage formatted as a usable signal, taking a derivative of a signal and producing an output proportional to how fast the input is changing, determining whether an input has reached a predetermined value by comparing two voltages and outputting either a one (1) or a zero (0), monitoring a voltage on a capacitor, and starting a timer on every rising edge.

According to some embodiments, a non-transitory storage medium storing a program for causing a computer to execute a wavelength interrogation method can include converting optical power from an input light source into an electrical current, converting output current of photodiodes to a voltage formatted as a usable signal, taking a derivative of a signal and producing an output proportional to how fast the input is changing, determining whether an input has reached a predetermined value by comparing two voltages and outputting either a one (1) or a zero (0), monitoring a voltage on a capacitor, and starting a timer on every rising edge.

Other Embodiments

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., ASIC) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, or a combination thereof (e.g., CPU, MPU, or the like), and may include a network of separate computers or separate processors to read out and execute the computer executable instructions. The computer executable instructions may be provided to the computerized configuration(s), for example, from a network or the storage medium. The storage medium may include, for example, one or more of a hard-disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A wavelength interrogation apparatus comprising:

an optical fiber with a fiber core and an interference pattern in the fiber core;

a photodiode or a photo-sensor to convert from a transmittance light of the optical fiber to an electrical signal; and an electrical circuit to generate a pulse with a predetermined duration, wherein the apparatus provides image acquisition at accurate start wavelength, and wherein the electrical circuit comprises:

a first amplifier;

a first differentiator or high-pass filter;

a comparator; and a multivibrator.

2. The wavelength interrogation apparatus according to claim 1, wherein the first differentiator comprises a differentiator amplifier configured to take a derivative of a signal and produces an output proportional to how fast an input is changing.

3. The wavelength interrogation apparatus according to claim 1, wherein the first differentiator comprises a high pass filter and charge pump amplifier configured to filter signals above a cut-off point frequency and generate short pulses at the output.

4. The wavelength interrogation apparatus according to claim 1, wherein the comparator determines whether an input has reached a predetermined value by comparing two voltages and outputting either a one (1) or a zero (0).

5. The wavelength interrogation apparatus according to claim 1, wherein the multivibrator is configured to monitor a voltage on a capacitor and start a timer on every rising edge.

6. The wavelength interrogation apparatus according to claim 1, wherein the first amplifier comprises a transimpedance amplifier configured to maintain stability by converting output current to a voltage formatted as a usable signal output.

7. The wavelength interrogation apparatus according to claim 6, wherein the transimpedance amplifier comprises at least an operational amplifier (op-amp), a feedback resister, and a feedback capacitor.

8. The wavelength interrogation apparatus according to claim 7, wherein the feedback capacitor provides a low-pass filter to attenuate noise.

9. The wavelength interrogation apparatus according to claim 7, wherein the transimpedance amplifier further comprises a resister divider to bias amplifier input above ground.

10. The wavelength interrogation apparatus according to claim 1, wherein the optical fiber comprises a fiber Bragg grating.

11. The wavelength interrogation apparatus according to claim 1, wherein the apparatus is part of a hermetically sealed temperature controlled package.

12. A wavelength interrogation method for the wavelength interrogation apparatus according to claim 1, the method comprising:

converting optical power from an input light source into an electrical current;

converting output current of one or more photodiodes to a voltage formatted as a usable signal;

taking a derivative of a signal and producing an output proportional to how fast the input is changing;

determining whether an input has reached a predetermined value by comparing two voltages and outputting either a one (1) or a zero (0);

monitoring a voltage on a capacitor; and starting a timer on every rising edge.

13. The method according to claim 12, further comprising starting the timer on every rising edge using artificial intelligence or machine learning.

14. The method according to claim 13, wherein the artificial intelligence is iterative.

15. A non-transitory storage medium storing a program for causing the wavelength interrogation apparatus according to claim 1, to execute a method for wavelength interrogation comprising:

converting optical power from an input light source into an electrical current;

converting output current of one or more photodiodes to a voltage formatted as a usable signal;

taking a derivative of a signal and producing an output proportional to how fast the input is changing;

determining whether an input has reached a predetermined value by comparing two voltages and outputting either a one (1) or a zero (0);

monitoring a voltage on a capacitor; and starting a timer on every rising edge.

16. The storage medium according to claim 15, wherein the method for wavelength interrogation further comprises starting the timer on every rising edge using artificial intelligence or machine learning.

17. The storage medium according to claim 16, wherein the artificial intelligence is iterative.

18. An intravascular imaging apparatus comprising:

a light source;

an interferometer;

a scanner; and a wavelength interrogator comprising:

an optical fiber with a fiber core and an interference pattern in the fiber core;

a first amplifier;

a first differentiator or high-pass filter;

a comparator; and a multivibrator, wherein the intravascular apparatus provides image acquisition at accurate start wavelength.

* * * * *